(12) United States Patent
Huang et al.

(10) Patent No.: US 10,039,538 B2
(45) Date of Patent: Aug. 7, 2018

(54) SENSING APPARATUS AND SURGICAL INSTRUMENT HAVING THE SAME

(71) Applicant: METAL INDUSTRIES RESEARCH & DEVELOPMENT CENTRE, Kaohsiung (TW)

(72) Inventors: Bing-Feng Huang, Kaohsiung (TW); Chin-Yu Chang, Taichung (TW); Yen-Ting Liu, Kaohsiung (TW); Wei-Ching Wang, Kaohsiung (TW); Chung-Fu Huang, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 322 days.

(21) Appl. No.: 14/981,954

(22) Filed: Dec. 29, 2015

(65) Prior Publication Data

US 2017/0156715 A1 Jun. 8, 2017

(30) Foreign Application Priority Data

Dec. 8, 2015 (TW) .............................. 104141124 A

(51) Int. Cl.
*A61B 17/02* (2006.01)
*G01L 5/00* (2006.01)
*A61B 34/30* (2016.01)
*A61B 17/00* (2006.01)
*A61B 90/00* (2016.01)

(52) U.S. Cl.
CPC .............. *A61B 17/02* (2013.01); *A61B 34/30* (2016.02); *A61B 90/06* (2016.02); *G01L 5/0038* (2013.01); *A61B 2017/00022* (2013.01); *A61B 2017/00119* (2013.01); *A61B 2090/061* (2016.02); *A61B 2090/064* (2016.02); *A61B 2090/065* (2016.02)

(58) Field of Classification Search
CPC ......... A61B 34/30–34/77; A61B 17/29–17/30; A61B 17/282; A61B 2017/00017; A61B 2017/2808; A61B 2018/00904
See application file for complete search history.

(56) References Cited

U.S. PATENT DOCUMENTS

| 3,785,381 A | 1/1974 | Laufe |
| 8,076,639 B2 | 12/2011 | Cooks et al. |
| 8,628,518 B2 | 1/2014 | Blumenkranz et al. |

(Continued)

*Primary Examiner* — Thaddeus Cox
(74) *Attorney, Agent, or Firm* — CKC & Partners Co., Ltd.

(57) ABSTRACT

A sensing apparatus is applicable to a surgical instrument having a clamping portion, a linkage rod member and an operating portion. The damping portion is used to damp a target. The sensing apparatus includes a touch sensor set, a force sensor, a displacement sensor and a processing device. The touch sensor set can sense a touch signal between the target and the clamping portion. The force sensor can sense a clamping force applied on the target. The displacement sensor can measure a displacement of the linkage rod member. The processing device includes a database, a processing unit and a comparison unit. The database stores reference curves of different reference objects. The processing unit can build an actual measurement curve of the target. The comparison unit can compare the actual measurement curve with each of the reference curves to obtain one of the reference curves corresponding to the actual measurement curve.

10 Claims, 5 Drawing Sheets

(56) References Cited

U.S. PATENT DOCUMENTS

2014/0171778 A1\* 6/2014 Tsusaka ............... A61B 5/6843
600/407
2017/0188792 A1\* 7/2017 Itkowitz ............. A61B 1/00006

\* cited by examiner

SENSING APPARATUS AND SURGICAL INSTRUMENT HAVING THE SAME

RELATED APPLICATIONS

This application claims priority to Taiwan Application Serial Number 104141124, filed Dec. 8, 2015, which is herein incorporated by reference.

BACKGROUND

Field of Invention

The present invention relates to a sensing apparatus and an application thereof.

Description of Related Art

In a general surgery process, an operative field is built to provide a doctor with a broader and clearer view of surgical range. However, for building the operative field, certain organs or soft tissues usually need to be supported or fixed. Therefore, when the doctor uses a surgical instrument or a mechanical arm to clamp or support the organs or soft tissues, it is important to control an operating force on the surgical instrument or the mechanical arm. Too big operating force often causes the organs or soft tissues to be damaged. On the contrary, too small operating force often causes the organs or soft tissues to slip off during the surgery process, thus interrupting the surgery.

SUMMARY

One object of the present invention is to provide a sensing apparatus and a surgical instrument having the sensing apparatus, which enables a doctor to timely adjust his operating force during the surgery process, so as to enhance safety and stability of the surgery.

According to the aforementioned object, a sensing apparatus is provided. The sensing apparatus is applicable to a surgical instrument. The surgical instrument includes a clamping portion, a linkage rod member and an operating portion. The linkage rod member is connected between the clamping portion and the operating portion, and the operating portion is used to control the clamping portion to clamp a target. The sensing apparatus includes a touch sensor set, a force sensor, a displacement sensor and a processing device. The touch sensor set is disposed on two opposite clamping surfaces of the clamping portion, in which the touch sensor set is configured to sense a touch signal between the target and the clamping portion. The force sensor is installed on the linkage rod member, in which the force sensor is configured to sense a clamping force applied on the target from the operating portion. The displacement sensor is installed on the linkage rod member, in which the displacement sensor is configured to start measuring a displacement of the linkage rod member according to the touch signal. The processing device is signally connected to the touch sensor set, the force sensor and the displacement sensor. The processing device includes a database, a processing unit and a comparison unit. The database is configured to store plural reference curves of different reference objects. The processing unit is configured to build an actual measurement curve of the target according to the clamping force and the displacement. The comparison unit is configured to compare the actual measurement curve with each of the reference curves to obtain one of the reference curves which is corresponding to the actual measurement curve.

According to the aforementioned object, a surgical instrument is provided. The surgical instrument includes a clamping portion, a linkage rod member, an operating end and a sensing apparatus. The linkage rod member is connected to the clamping portion. The operating end is connected to the linkage rod member to displace the linkage rod member to control the clamping portion to clamp a target. The sensing apparatus is applicable to a surgical instrument. The surgical instrument includes a clamping portion, a linkage rod member and an operating portion. The linkage rod member is connected between the clamping portion and the operating portion, and the operating portion is used to control the clamping portion to clamp a target. The sensing apparatus includes a touch sensor set, a force sensor, a displacement sensor and a processing device. The touch sensor set is disposed on two opposite clamping surfaces of the clamping portion, in which the touch sensor set is configured to sense a touch signal between the target and the clamping portion. The force sensor is installed on the linkage rod member, in which the force sensor is configured to sense a clamping force applied on the target from the operating portion. The displacement sensor is installed on the linkage rod member, in which the displacement sensor is configured to start measuring a displacement of the linkage rod member according to the touch signal. The processing device is signally connected to the touch sensor set, the force sensor and the displacement sensor. The processing device includes a database, a processing unit and a comparison unit. The database is configured to store plural reference curves of different reference objects. The processing unit is configured to build an actual measurement curve of the target according to the clamping force and the displacement. The comparison unit is configured to compare the actual measurement curve with each of the reference curves to obtain one of the reference curves which is corresponding to the actual measurement curve.

According to an embodiment of the present invention, the displacement is a distance of the linkage rod member moving from an initial position to a displaced position, and the initial position is a location of the linkage rod member when the touch signal is first generated.

According to an embodiment of the present invention, the actual measurement curve represents a relationship between the clamping force applied on the target and a deformation value of the target deformed by the clamping force.

According to an embodiment of the present invention, each of the reference curves represents a relationship between a clamping force applied on the reference object and a deformation value of the reference object deformed by the clamping force applied on the reference object.

According to an embodiment of the present invention, the reference curves have failure points respectively, and the failure points are corresponding to the reference objects respectively. The processing device further includes a warning unit, when the clamping force applied on the target is greater than the failure point of the corresponded reference object, the warning unit generates an alarm signal.

It can be known from the aforementioned embodiments of the present invention that, the present invention can enable doctors to identify the types of soft tissues which is a clamped target, so as to obtain information of an operating force applied on the clamped target, and tissue characteristics and deformation value of the clamped target, etc. Therefore, the doctors can adjust his/or her operating force to ensure that the clamped target is kept in an optimum operating condition, thus enhancing the quality and stability of the surgery.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
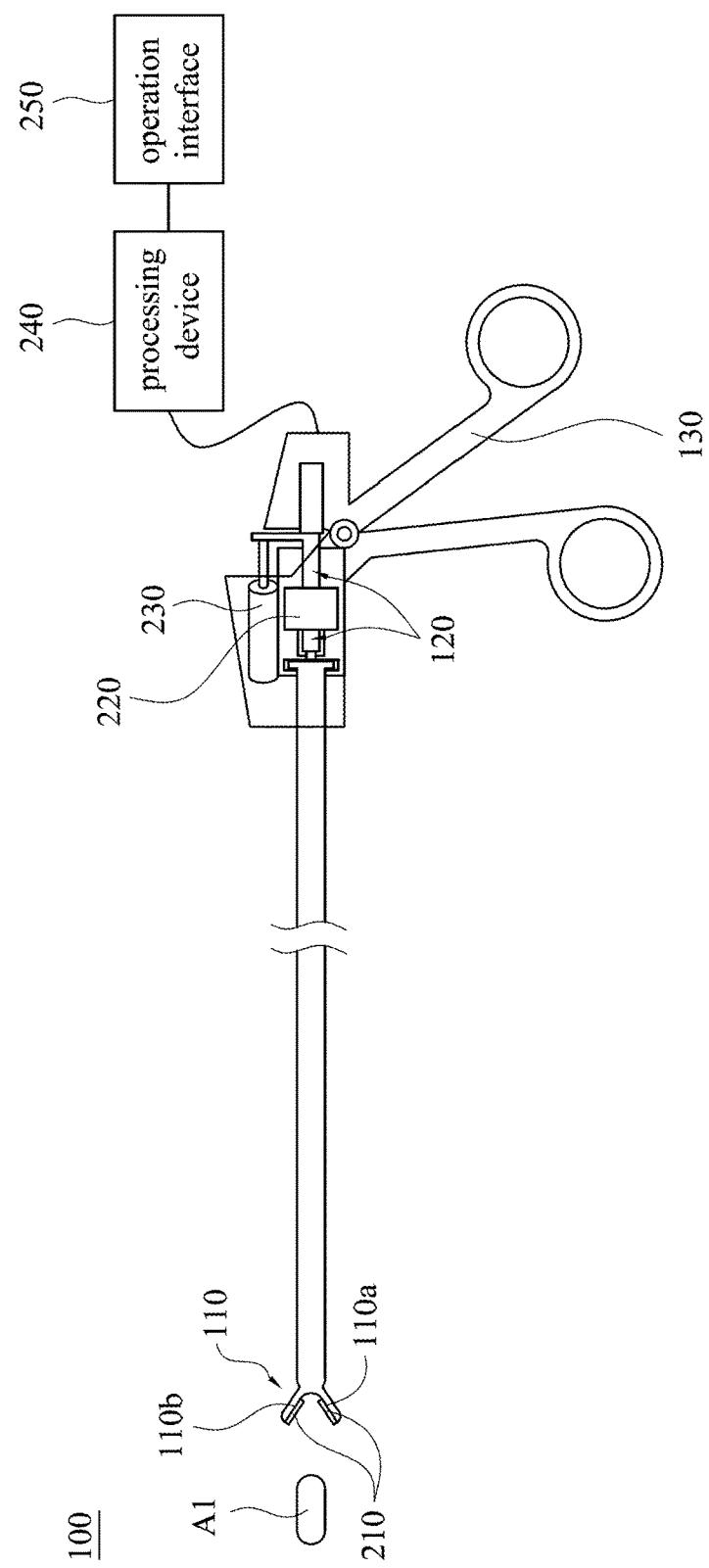
FIG. 1 is a schematic structural diagram showing a surgical instrument in accordance with an embodiment of the present invention.

Reference will now be made in detail to the present embodiments of the invention, examples of which are illustrated in the accompanying drawings. Wherever possible, the same reference numbers are used in the drawings and the description to refer to the same or like parts.

Figure 2:
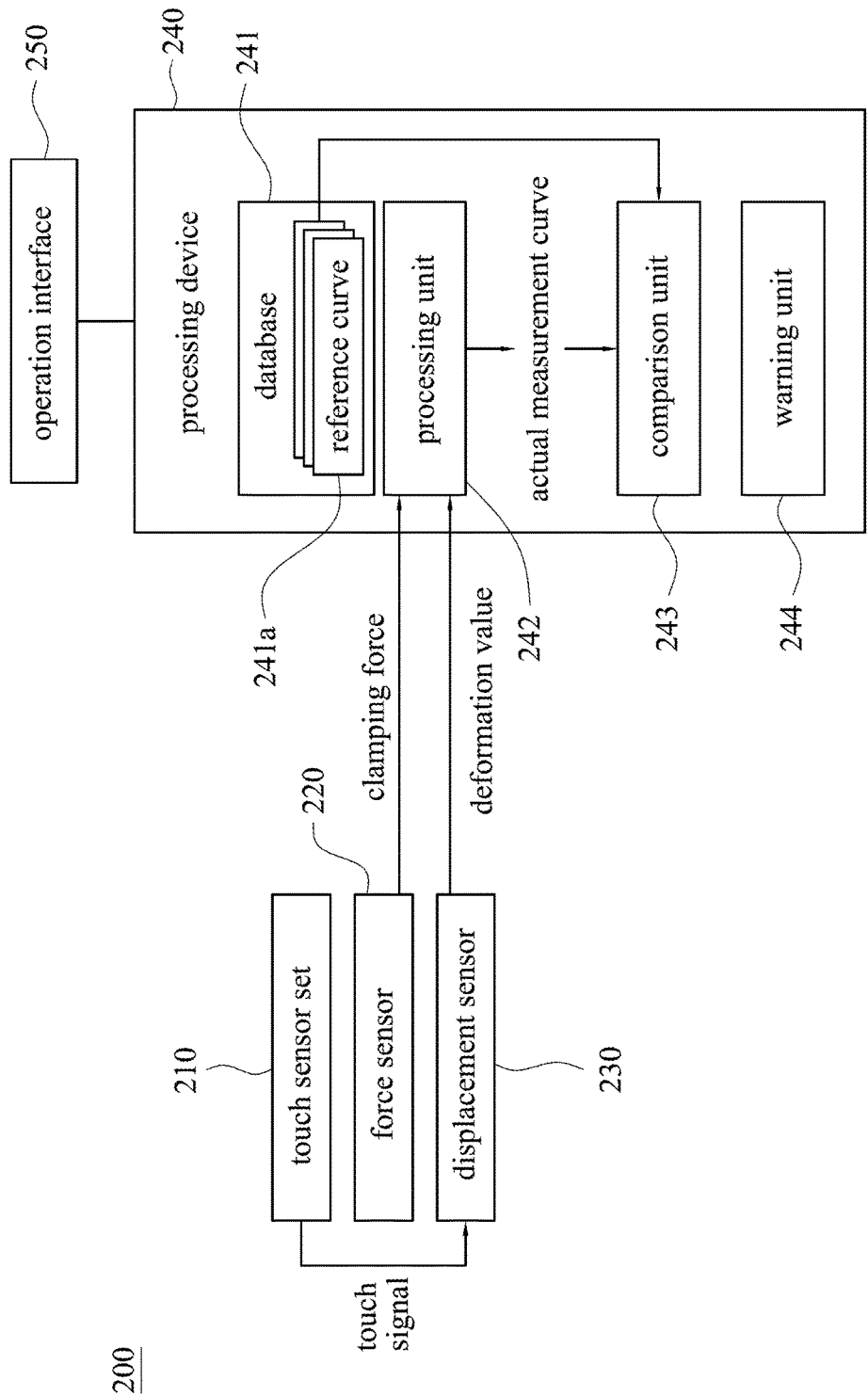
FIG. 2 is a schematic diagram showing a sensing apparatus in accordance with an embodiment of the present invention.

Simultaneously referring to FIG. 1 and FIG. 2, FIG. 1 is a schematic structural diagram showing a surgical instrument 100 in accordance with an embodiment of the present invention, and FIG. 2 is a schematic diagram showing a sensing apparatus 200 in accordance with an embodiment of the present invention. The surgical instrument 100 of the present embodiment is a manual instrument, a mechanical arm controlled by a computer or a surgical robot. The surgical instrument 100 mainly includes a clamping portion 110, a linkage rod member 120, an operating portion 130 and the sensing apparatus 200. The linkage rod member 120 is connected between the clamping portion 110 and the operating portion 130. The operating portion 130 is used to displace the linkage rod member 120 to control the clamping portion to clamp a target A1. The "target A1" can be referred to as a soft tissue or an organ of a human body or an animal, but embodiments of the present invention are not limited thereto.

Referring to FIG. 1 and FIG. 2 again, the sensing apparatus 200 is mainly installed between the clamping portion 110 and the operating portion 130. In the present embodiment, the sensing apparatus 200 mainly includes a touch sensor set 210, a force sensor 220, a displacement sensor 230, a processing device 240 and an operation interface 250. The touch sensor set 210 is disposed on two opposite clamping surfaces 110a and 110b of the clamping portion 110. The touch sensor set 210 is configured to sense a touch signal between the target A1 and the clamping portion 110. In some embodiments, the touch sensor set 210 includes one micro electromechanical sensor which contacts both of the clamping surfaces 110a and 110b. In other embodiments, the touch sensor set 210 includes two or more micro electromechanical sensors which are respectively disposed on the clamping surfaces 110a and 110b. In some examples, the touch sensor set 210 can be a pressure sensor or an optical sensor. It is noted that, because the touch sensor set 210 is disposed on the two clamping surfaces 110a and 110b, the touch sensor set 210 does not generate the touch signal until the clamping surfaces 110a and 110b simultaneously touch the target A1.

Referring to FIG. 1 and FIG. 2 again, the force sensor 220 and the displacement sensor 230 are installed on the linkage rod member 120. When a user operates the operating portion 130 to control the linkage rod member 120 to clamp the target A1, the force sensor 220 can sense an application force from the user, and the displacement sensor 230 can measure a displacement of the linkage rod member 120. In other words, the force sensor 220 is configured to sense a clamping force applied on the target A1 from the operating portion 130. The displacement sensor 230 is configured to measure a distance of the linkage rod member 120 moving from an initial position to a displaced position while clamping portion 110 is clamping the target A1. The "initial position" is referred to as a location of the linkage rod member 120 when the touch signal is first generated. In other words, the "initial position" is determined by a moment when the target A1 touches the touch sensor set 210 located on the two clamping surfaces 110a and 110b. After the touch signal is first generated by the touch sensor set 210, the operating portion 130 continues to control the clamping portion 110 to displace the linkage rod member 120 to the position at which the target A1 is not under force. The "displaced position" is referred to as a location of the displaced linkage rod member 120. Therefore, the displacement of the linkage rod member 120 is a distance of the linkage rod member 120 moving from the initial position to the displaced position. In one embodiment, the displacement sensor 230 is a linear variable differential transformer (LVDT).

Figure 3:
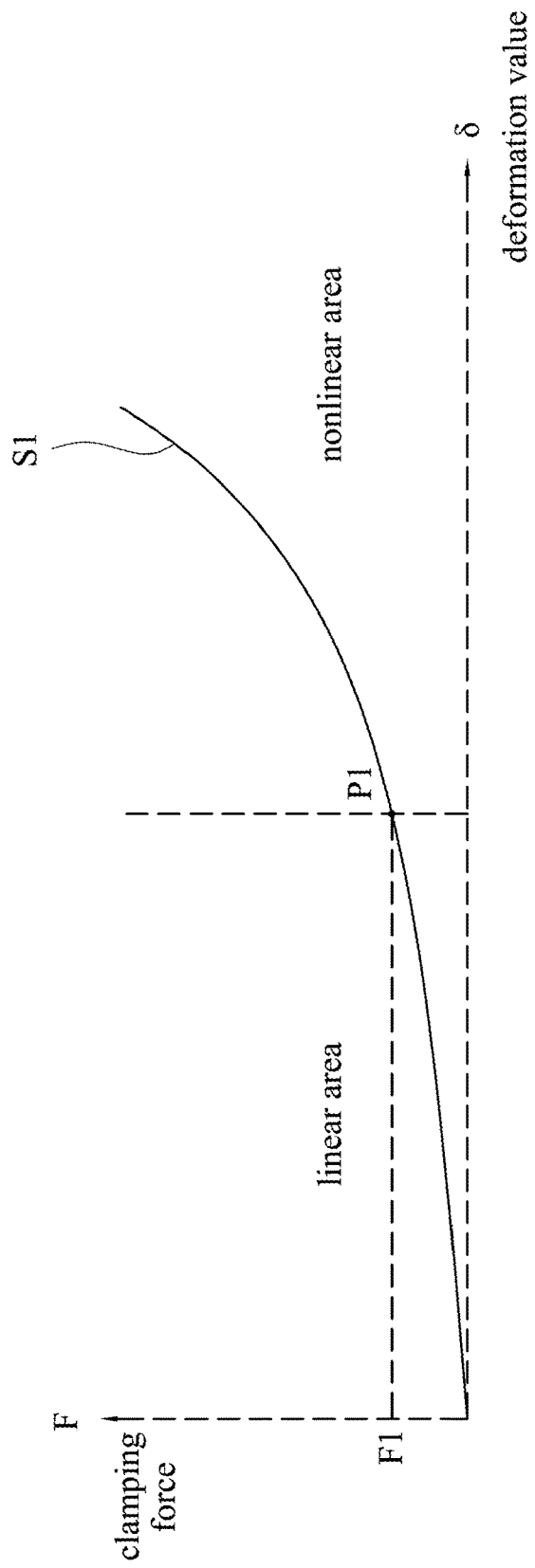
FIG. 3 is a schematic diagram showing a reference curve in accordance with an embodiment of the present invention.

As shown in FIG. 2, the processing device 240 is signally connected to the touch sensor set 210, the force sensor 220 and the displacement sensor 230. The processing device 240 is electrically connected to the operation interface 250. The processing device 240 mainly includes a database 241, a processing unit 242, a comparison unit 243 and a warning unit 244. The database 241 stores plural reference curves 241a of different reference objects. The "reference objects" can be referred to as different soft tissues or organs of a human body or an animal. Simultaneously referring to FIG. 3, FIG. 3 is a schematic diagram showing one of the reference curves in accordance with an embodiment of the present invention. Curve S1 shown in FIG. 3 is one of the reference curves which represents a relationship between a clamping force applied on the reference object and a deformation value of the reference object deformed by the clamping force. In the present embodiment, different reference objects have respective reference curves 241a.

Figure 4:
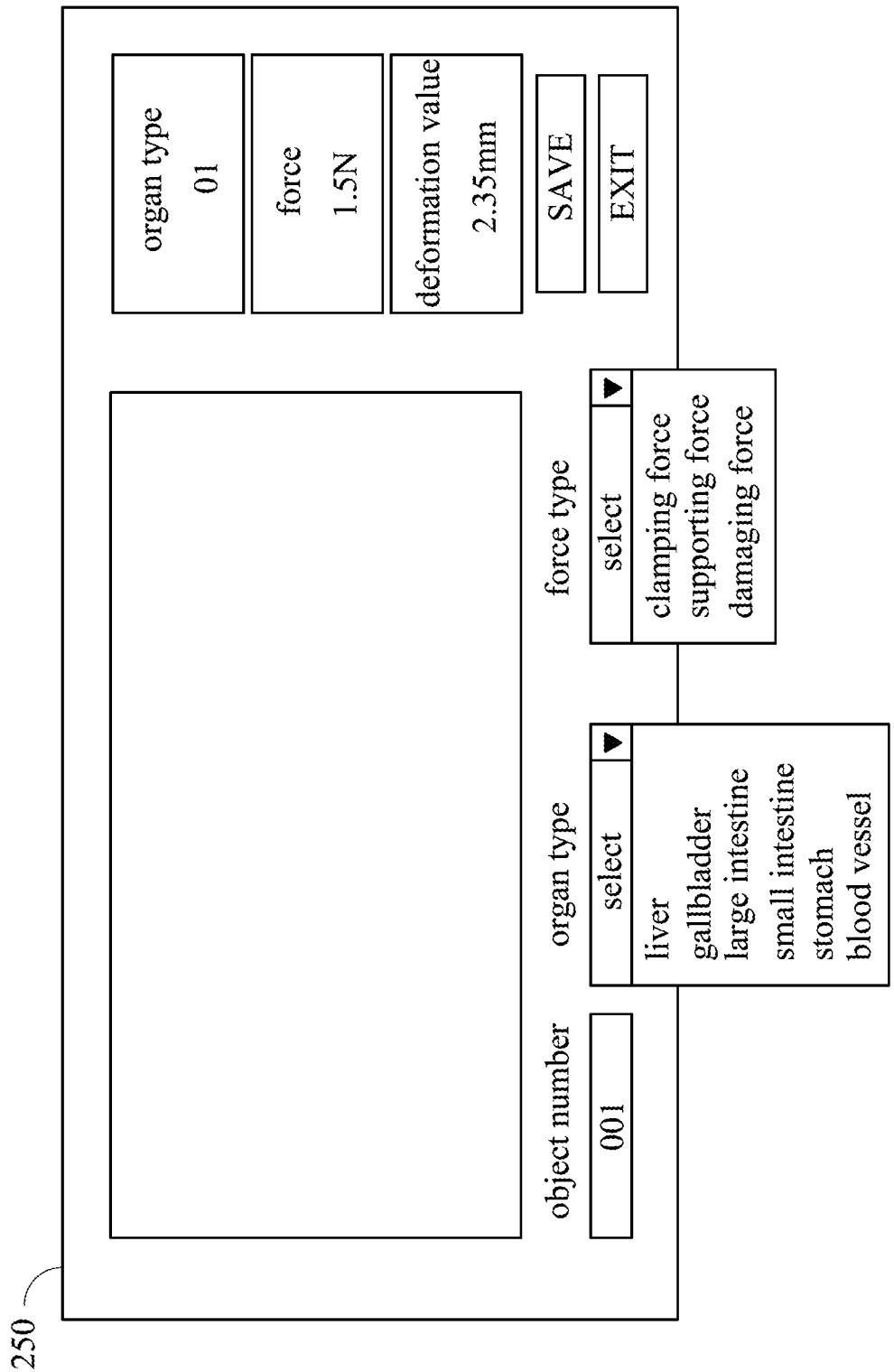
FIG. 4 is a schematic diagram showing an operation interface in accordance with an embodiment of the present invention.

In some embodiments, the reference curves 241a can be built from professional doctors' experiences by using the surgical instrument 100 of the present invention, or based on the current research of tissue characteristics of each reference object. Simultaneously referring to FIG. 1, FIG. 2 and FIG. 4, FIG. 4 is a schematic diagram showing an operation interface 250 in accordance with an embodiment of the present invention. In one example, the professional doctors can use the surgical instrument 100 of the present invention to clamp different reference objects such as different organs or soft tissues, thereby building the reference curves 241a corresponding to the organs or the soft tissues respectively. Before operating the operating portion 130 to control the clamping portion 110 to clamp the reference objects, the professional doctors can first set a type of an organ or a type of force. Then, the professional doctors use the surgical instrument 100 to clamp one of the reference objects to obtain a clamping force and a displacement corresponding to the reference object via the touch sensor set 210, the force sensor 220 and the displacement sensor 230. Thereafter, the processing unit 242 of the processing device 240 can respectively transfer the displacement into a deformation value which is corresponding to the reference object, thereby building an actual measurement curve corresponding to the reference object. The "actual measurement curve of the reference object" can be referred to as a relationship between the clamping force applied on the reference object and the deformation value of the reference object deformed by the clamping force applied on the reference object. Therefore, the professional doctors can further save different actual measurement curves respectively corresponding to the reference objects into the database 241 as reference curves 241a, thereby providing other novices with reference in surgery process or setting up operating parameters of a mechanical arm.

In practical operation, when operating the surgical instrument 100, other users (e.g. the novices) can operate the operating portion 130 to displace the linkage rod member 120 to clamp the target A1, thereby obtaining a clamping forces applied on the target A1 and a displacement of the linkage rod member 120 via the force sensor 220 and the displacement sensor 230. After obtaining the clamping force applied on the target A1 and the displacement of the linkage rod member 120, the processing unit 242 can transfer the displacement of the linkage rod member 120 into a deformation value of the target A1, and then build an actual measurement curve of the target A1. Furthermore, the "actual measurement curve of the target A1" can be referred to as a relationship between the clamping force applied on the target A1 and the deformation value of the target A1 deformed by the clamping force applied on the target A1.

After the processing unit 242 builds the actual measurement curve of the target A1, the comparison unit 243 can further compare the actual measurement curve with each of the reference curves 241a to find out one of the reference curves from the database 241 which is corresponding to the actual measurement curve. After the comparison unit 243 finds out the reference curve 241a which is corresponding to the actual measurement curve, the corresponded reference curve 241a can be shown on the operation interface 250 as a comparison result to the users for reference. Furthermore, the reference curve 241a found out by the comparison unit 243 from the database can represent one of the reference objects which is the same organ or soft tissue as the target A1. Therefore, the users can identify which types the target A1 is and what tissue characteristic the target A1 has by the comparison result.

In some embodiments, as shown in FIG. 3, each of the reference curves 241a has a failure point P1. The "failure point P1" is referred to as a damage threshold which is corresponding to a clamping force F1 applied on the reference object. When the clamping force applied on the target A1 is greater than that at the failure point P1 of the corresponded reference object, the warning unit generates an alarm signal to the user.

Figure 5:
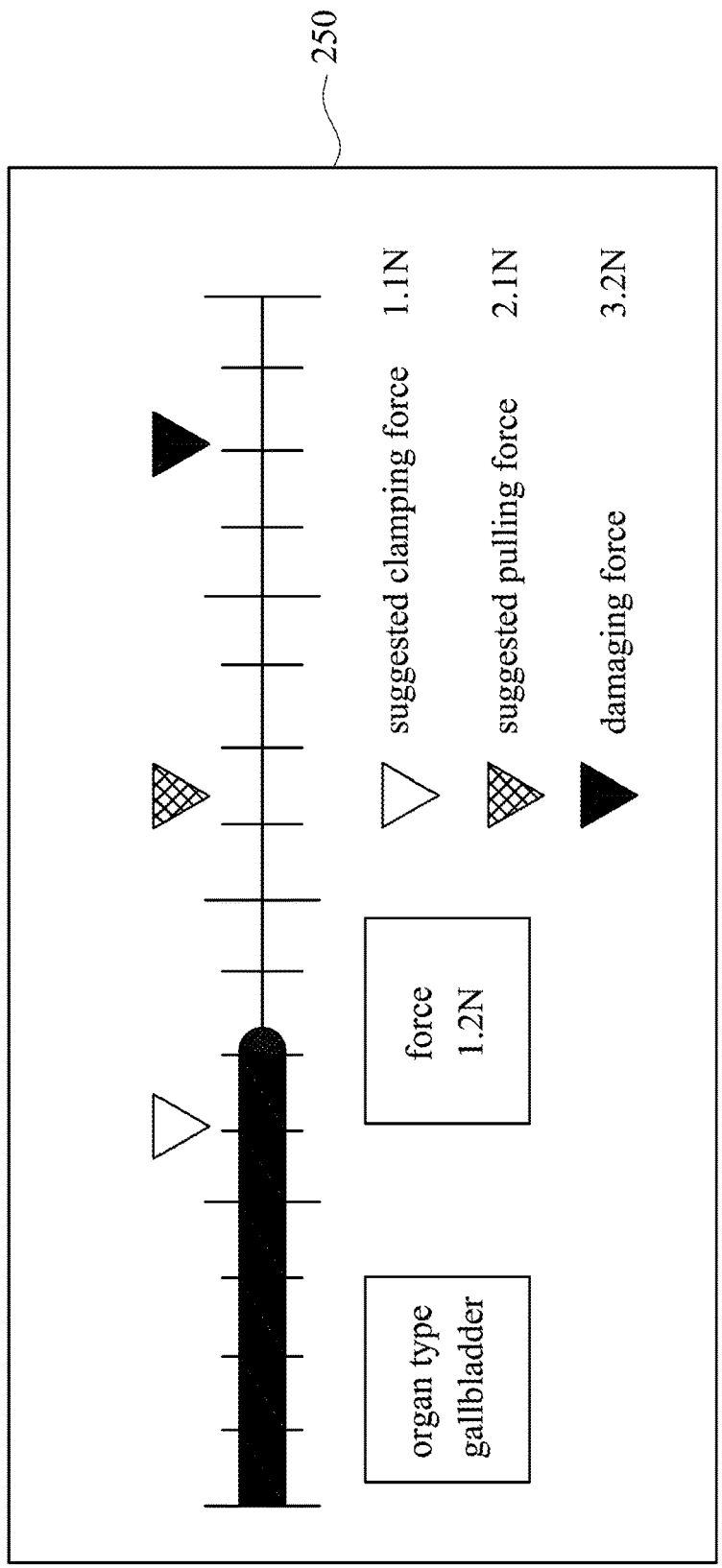
FIG. 5 is a schematic diagram showing a comparison result in accordance with an embodiment of the present invention.

In one example, besides the reference curve 241a, the comparison result can also be shown as data. Referring to FIG. 5, FIG. 5 is a schematic diagram showing a comparison result in accordance with an embodiment of the present invention. After the comparison unit 243 finds out the reference object which is corresponding to the target A1, the operation interface 250 can show information related to corresponded the reference object to the user. For example, a type of the organ or soft tissue, a force applied on the target A1, a suggested clamping force, a suggested pulling force, a damaging force, etc. Therefore, the user can control the force when operating the surgical instrument 100, so as to prevent danger from applying too much force on the target A1 during surgery process. It is noted that the data shown in FIG. 5 is merely used for explanation, and other embodiments of the present invention are not limited thereto.

Similarly, the sensing apparatus 200 can also be installed on common a mechanical arm to connected to its original operating portion, linkage rod member, and clamping portion, thereby obtaining a comparison result, for example, which types the target A1 is and what tissue characteristic the target A1. Therefore, the user can set parameters of the mechanical arm according to the comparison result to adjust an optimum operating force, so as to ensure the surgical operation performed smoothly.

It can be known from the aforementioned embodiments of the present invention that, the present invention can enable doctors to identify the types of soft tissues which is a clamped target, so as to obtain information of an operating force applied on the clamped target, and tissue characteristics and deformation value of the clamped target, etc. Therefore, the doctors can adjust his/her operating force to ensure that the clamped target is kept in an optimum operating condition, thus enhancing the quality and stability of the surgery.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A sensing apparatus applicable to a surgical instrument, wherein the surgical instrument comprises a clamping portion, a linkage rod member and an operating portion, the linkage rod member is connected between the clamping portion and the operating portion, and the operating portion is used to control the clamping portion to clamp a target, wherein the sensing apparatus comprises:
   a touch sensor set disposed on two opposite clamping surfaces of the clamping portion, wherein the touch sensor set senses a touch signal when the target touches the clamping portion;
   a force sensor installed on the linkage rod member, wherein the force sensor senses a clamping force applied on the target from the operating portion when the target touches the clamping portion;
   a displacement sensor installed on the linkage rod member and signally connected to the touch sensor set, wherein the displacement sensor starts measuring a displacement of the linkage rod member when receiving the touch signal; and
   a processing device comprising:
      a database in which a plurality of reference curves of different reference objects are stored;
      a processing circuit signally connected to the force sensor and the displacement sensor, wherein the processing circuit builds an actual measurement curve of the target according to the clamping force and the displacement, and a comparison circuit signally connected to the processing circuit and the database, wherein the comparison circuit compares the actual measurement curve with each of the reference curves to obtain one of the reference curves which is corresponding to the actual measurement curve.

2. The sensing apparatus of claim 1, wherein the displacement is a distance of the linkage rod member moving from an initial position to a displaced position, and the initial position is a location of the linkage rod member when the touch signal is first generated.

3. The sensing apparatus of claim 1, wherein the actual measurement curve represents a relationship between the clamping force applied on the target and a deformation value of the target deformed by the clamping force.

4. The sensing apparatus of claim 1, wherein each of the reference curves represents a relationship between a clamping force applied on the reference object and a deformation value of the reference object deformed by the clamping force applied on the reference object.

5. The sensing apparatus of claim 4, wherein
the reference curves have failure points respectively, and the failure points are corresponding to the reference objects respectively; and
the processing device further comprises a warning circuit, wherein when the clamping force applied on the target is greater than the failure point of the corresponded reference object, the warning circuit generates an alarm signal.

6. A surgical instrument, comprising:
a clamping portion;
a linkage rod member connected to the clamping portion;
an operating end connected to the linkage rod member to displace the linkage rod member to control the clamping portion to clamp a target, and
a sensing apparatus comprising:
a touch sensor set disposed on two opposite clamping surfaces of the clamping portion, wherein the touch sensor set senses a touch signal when the target touches the clamping portion;
a force sensor installed on the linkage rod member, wherein the force sensor senses a clamping force applied on the target from the operating end when the target touches the clamping portion;
a displacement sensor installed on the linkage rod member and signally connected to the touch sensor set, wherein the displacement sensor starts measuring a displacement of the linkage rod member when receiving the touch signal; and
a processing device comprising:
a database in which a plurality of reference curves of different reference objects are stored;
a processing circuit signally connected to the force sensor and the displacement sensor, wherein the processing circuit builds an actual measurement curve of the target according to the clamping force and the displacement, and
a comparison circuit signally connected to the processing circuit and the database, wherein the comparison circuit compares the actual measurement curve with each of the reference curves to obtain one of the reference curves which is corresponding to the actual measurement curve.

7. The surgical instrument of claim 6, wherein the displacement is a distance of the linkage rod member moving from an initial position to a displaced position, and the initial position is a location of the linkage rod member when the touch signal is generated.

8. The surgical instrument of claim 6, wherein the actual measurement curve represents a relationship between the clamping force applied on the target and a deformation value of the target deformed by the clamping force.

9. The surgical instrument of claim 6, wherein each of the reference curves represents a relationship between a clamping force applied on the reference object and a deformation value of the reference object deformed by the clamping force applied on the reference object.

10. The surgical instrument of claim 9, wherein
the reference curves have failure points respectively, and the failure points are corresponding to the reference objects respectively; and
the processing device further comprises a warning circuit, wherein when the clamping force applied on the target is greater than the failure points of the corresponded reference object, the warning circuit generates an alarm signal.

* * * * *